United States Patent [19]

Tuominen

[11] 4,454,112

[45] Jun. 12, 1984

[54] SUNSCREEN COMPOSITION CONTAINING TOCOPHEROL ACETYLSALICYLATE

[75] Inventor: Francis W. Tuominen, Minneapolis, Minn.

[73] Assignee: Henkel Corporation, Minneapolis, Minn.

[21] Appl. No.: 358,557

[22] Filed: Mar. 16, 1982

Related U.S. Application Data

[63] Continuation of Ser. No. 865,081, Dec. 27, 1977, abandoned.

[51] Int. Cl.$^3$ ............................................. A61K 7/44
[52] U.S. Cl. ..................................... 424/60; 424/284; 549/410
[58] Field of Search .................. 424/284, 60; 549/410

[56] References Cited

U.S. PATENT DOCUMENTS

| | | | |
|---|---|---|---|
| 3,177,120 | 4/1965 | Black et al. | 424/60 |
| 4,144,325 | 3/1979 | Voyt | 424/60 |
| 4,154,823 | 5/1979 | Schutt | 424/60 |

FOREIGN PATENT DOCUMENTS 2314722 6/1975 France .

OTHER PUBLICATIONS

Nakamura et al., Chem. Abstract, 76, 34105x, (1972).
Nakamura et al., Chem. Abstract, 84, 25708j, (1976).

Primary Examiner—Nicky Chan
Attorney, Agent, or Firm—Patrick J. Span; Ernest G. Szoke

[57] ABSTRACT

The present invention describes the preparation and utilization of tocopherol acetylsalicylate compounds which have utility for lessening erythema.

2 Claims, No Drawings

SUNSCREEN COMPOSITION CONTAINING TOCOPHEROL ACETYLSALICYLATE

This is a continuation of application Ser. No. 865,081, filed Dec. 27, 1977, now abandoned.

BACKGROUND OF THE INVENTION

1. Field of the Invention

The present invention describes the formation and use of esters containing a tocopherol (particularly Vitamin E) and a acetylsalicyclic acid structure.

2. Description of the Art

Various tocopherol derivatives are known to exist. For instance U.S. Pat. No. 2,231,125 issued to Karrer on Feb. 11, 1941 describes the preparation of stearic and oleic esters of tocopherol. Karrer discusses the introduction of allyl groups into tocopherol in U.S. Pat. No. 2,245,480 issued June 10, 1941.

The preparation of tocopherol succinates by Baxter et al. is found in U.S. Pat. No. 2,358,046 issued Sept. 22, 1944. The preparation of crystalline dl-alpha-tocopheral-p-nitro-benzoic acid esters is described in U.S. Pat. No. 2,393,134 issued to Aeschlimann Jan. 15, 1946. The process of esterifying tocopherols with acyl halides is set out in U.S. Pat. No. 2,486,541 issued to Baxter et al. on Nov. 1, 1949.

Water soluble tocopherol derivatives prepared by esterifying tocopherol acid esters with polyethylene glycol are described in U.S. Pat. No. 2,680,749 to Cawley et al. on June 8, 1954. Among the tocopherol acid esters described by Cawley as suitable for condensation with the polyethylene glycol include: succinates, citraconates, methyl citraconates, itaconates maleates, glutaconates, and phthalates.

The preparation of tocopherol ascorbates is described by Spanel in U.S. Pat. No. 3,151,127 issued Sept. 29, 1964. U.S. Pat. No. 3,869,477 issued Mar. 4, 1975 to Schindo et al. describes the preparation of tocopherol-p-chlorophenoxyisobutyric acid esters which are stated to have an affect on arteriosclerosis and of affecting betterment of lipid metabolism. Vitamin A acid esters of tocopherol are described in U.S. Pat. No. 3,878,202 issued Apr. 15, 1975 to Fukawa et al. Cholesterol esters of acetylsalicylate were stated to have been prepared by Montignie in the Bull. soc. chim. 49, 1852–1853 (1931).

To date, other researchers have not explored the utilization and preparation of tocopherol acetylsalicylates. Throughout the specification and claims percentages and ratios are by weight and temperatures are in degrees Celsius, unless otherwise indicated.

SUMMARY OF THE INVENTION

The present invention is concerned with tocopherol acetylsalicylate as novel compounds. Most preferably the tocopherol acetylsalicylate is alpha-tocopherol orthoacetylsalicylate.

The tocopherol acetylsalicylates described herein have been found useful as sunscreening agents in that the subject compounds absorb ultraviolet light. The present compounds also have utility in that oral administration of the compounds will provide sustained release of acetylsalicyclic acid in mammals.

DETAILED DESCRIPTION OF THE INVENTION

The present invention as previously stated relates to the preparation of tocopherol acetylsalicylates. The preferred form of tocopherol is that commonly denominated as alpha-tocopherol. The alpha-tocopherol may be either natural or synthetically produced. Other tocopherols may also be used in the present invention including the beta, gamma, and delta forms.

The acetylsalicylate portion of the novel ester is conveniently provided by an acetylsalicyloyl halide in particular, acetylsalicyloyl chloride. The preferred structure for the acetylsalicylate is that of the ortho isomer.

The preparation of the tocopherol acetylsalicylate is conveniently carried out by reacting equal molar quantities of the tocopherol and acetylsalicyloyl chloride using toluene as a solvent. While the reaction to the tocopherol and the acetylsalicyloyl chloride is conveniently carried out on an equal molar basis, it is also possible to include excess amounts of one ingredient or the other to ensure completion of the reaction. Thus it is often desirable to include a slight excess of the acetylsalicyloyl chloride due to the fact that the tocopherol is the more expensive reactant.

To further facilitate completion of the reaction of the tocopherol and the acetylsalicyloyl chloride, dimethyl aniline is added to the reaction mixture to function as a hydrogen chloride scavenger. The dimethyl aniline may be added in a slight molar excess to the amount of hydrogen chloride which forms during the reaction. The dimethyl aniline hydrochloride so formed is extracted with sufficient water to ensure its removal.

The tocopherol acetylsalicylate in the toluene solution is then treated with a drying agent such as calcium sulfate to remove the water. The drying agent is then filtered out of the mixture of toluene and product. The toluene is then distilled off using reduced pressure and a temperature of about 50 degrees Celsius. The residue is then purified by trituration with acetonitrile to remove any unreacted materials. Any excess acetonitrile is then removed from the reaction product at slightly reduced pressure.

The tocopherol acetylsalicylate may be further purified by successive triturations using the acetonitrile until the tocopherol acetylsalicylate reaches the desired degree of purity. It will be recognized that the degree of purity for oral usage should be higher than that for its topical use as a sunscreen.

The compounds of the present invention as previously stated, have two beneficial uses. The first use is that of the compound as a sunscreening agent to absorb a selected portion of the ultraviolet spectrum. Secondly, the compounds of the present invention may be utilized in medicinal preparation as a sustained release agent of acetylsalicylate ions or aspirin.

In the first utility of the present invention, namely that of ultraviolet absorption, the tocopherol acetylsalicylate is found to absorb ultraviolet radiation having a maximum absorbence at 288 nanometers. At one-half of the absorbtion maximum the wave lengths at which the compound is absorbing ultraviolet radiation is from 265 to 310 nanometers. The compositions of the present invention are thus useful in absorbing a portion of the intense ultraviolet radiation at the specified wavelengths. That is, it must be remembered that the purpose of any sunscreening agent (UV absorber) is not to prevent the suns ultraviolet radiation from reaching the skin, but to reduce its intensity so as to enable the skin to build up its own protection against exposure by means of tanning. Moreover, it has been suggested that ultraviolet radiation has the ability to induce skin carcinoma over a substantial portion of the ultraviolet spectrum. It is thus suggested that the use of the tocopherol acetylsalicylate protects the skin from overdoses of ultraviolet radiation within the aforementioned wave length band.

It has also been noted with respect to the use of the tocopherol acetylsalicylate as a sunscreen that there are purported effects of the use of tocopherols as skin conditioning agents. That is, the use of tocopherol and in particular alpha-tocopherol, that the skin retains a youthful appearance for a longer period of time than skin not so treated. This is particularly important when considering that the tocopherol acetylsalicylates of the present invention are suggested for use under adverse climatic conditions. That is the compounds of the present invention when used as a sunscreen, not withstanding the effect of absorbing ultraviolet light, should provide skin care benefits due to the tocopherol portion of the molecule. Additionally, the tocopherol acetylsalicylate is not readily washed away from the skin and thus repeated applications of a sunscreen formulation containing the tocopherol acetylsalicylate are not frequently needed during sunbathing.

The desired effect of the second suggested utility for the tocopherol acetylsalicylate lies primarily in the fact that it has been widely reported that ordinary aspirin causes gastrointestinal irritation and bleeding, thus causing or aggravating ulcerated conditions. It is believed that when aspirin in its conventional form is taken orally that is dissolves in the stomach presenting concentrated areas of acetylsalicylic acid in the gastrointestinal environment. A solution of this problem of stomach irritation is to present the aspirin in such a form that it is slowly hydrolyzed to the active acid. The effect of introducing the acetylsalycilic acid in the form of tocopherol acetylsalicylate is to yield a sustained release of the acetylsalicylate in the stomach or the blood. Slow release, followed by uptake in the blood of the tocopherol acetylsalicylate minimizes the concentration in the stomach of the acid form. The dosage required of the tocopherol acetylsalicylate is simply a molar extension of that used in conventional aspirin products. Preparation of this aspirin substitute would follow conventional aspirin products with the exception of using the ester of the present invention.

Additionally, it must be remembered when using a biologically active form of tocopherol acetylsalicylate that not only will the aspirin be made available for medicinal purposes, but that the tocopherol will also be available as Vitamin E or a precursor thereof. Thus another distinct advantage of the present invention is that patients requiring both aspirin and Vitamin E supplementation in the diet will only need to take one form of medication as opposed to successive treatments. It will also be recognized that tocopherol acetylsalicylate could be introduced into the patient by injection.

The following are examples related to the present invention:

EXAMPLE I

Preparation of Alpha-Tocopherol Orthoacetylsalicylate 50 grams of alpha-tocopherol and 25 milliliters of ortho acetylsalicyloyl chloride are added to a flask utilizing 400 milliliters of toluene as a solvent. The reaction flask and the toluene were previously dried to remove any moisture present in the system. To the reaction mixture 23 milliliters of dimethyl aniline is added to scavenge the hydrogen chloride liberated during the esterification.

The formation of the alpha-tocopherol orthoacetylsalicylate is carried out by refluxing the mixture described above for a period of one hour. At the end of one hour the reaction is essentially complete and the dimethyl aniline hydrochloride formed during the reaction is removed by water extraction. The water extraction is carried out by using three successive 200 milliliter washes in a separatory funnel. The non-aqueous phase containing the toluene and the alpha-tocopherol orthoacetylsalicylate is retained and dried with calcium sulphate to remove any water remaining.

The reaction mixture following the drying steps described above is then filtered in a Buchner funnel to remove the calcium sulphate. The toluene is then removed by vacuum distillation using an aspirator. The mixture obtained following removal of the toluene is a light brown oily liquid. This residue is then triturated with acetonitrile to remove any unreacted tocopherol. The amount of acetonitrile utilized is about 10 milliliters per gram of residue.

Following removal of the excess acetonitrile and the by-products of the reaction, 41 grams of a mixture containing the alpha-tocopherol acetylsalicylate are obtained. The purity of the desired reaction product is greater than 90%. The remaining impurity is largely acetylsalicylic acid which is not at all undesirable in the orally administered products as it may be neutralized and left in the dosage. That is the end product may be prepared to comprise both a large portion of the tocopherol acetylsalicylate for delayed release and a smaller amount of readily accessible aspirin for fast relief.

The product may be further purified if desired by successive triturations of the tocopherol acetylsalicylate with acetonitrile. In most cases the additional trituration technique is unnecessary.

Similar products may be prepared and utilized in the succeeding examples from beta, gamma, and delta tocopherols.

EXAMPLE II

Utilization of the Alpha-Tocopherol Orthoacetylsalicylate

The product of Example I is formulated in a sunscreen lotion having the following composition:
alpha-tocopherol orthoacetylsalicylate 1%
oleyl alcohol 10%
mineral oil 89%

The foregoing formulation is found effective in reducing the amount of ultraviolet radiation reaching the skin when applied at a level of 0.25 grams per square centimeter of skin surface. The wave length of the ultraviolet radiation absorbed by the composition is determined to have an absorption maximum at 288 nanometers and a band width at one-half of the absorbtion maximum of 45 nanometers.

What is claimed is:

1. A method of reducing the amount of ultraviolet radiation receiving the skin which includes contacting the skin with an effective amount of tocopherol acetylsalicylate to reduce the amount of the ultraviolet radiation reaching the skin.

2. A sunscreen composition containing 1% tocopherol acetylsalicylate, 10% oleyl alcohol, and 89% mineral oil.

* * * * *